(12) United States Patent
Mottate

(10) Patent No.: US 6,305,932 B1
(45) Date of Patent: Oct. 23, 2001

(54) ORTHODONTIC ELEMENT AND MANUFACTURING METHOD

(75) Inventor: Mikio Mottate, Fukushima (JP)

(73) Assignee: Tomy Incorporated, Fukushima (JP)

( * ) Notice: Subject to any disclaimer, the term of this patent is extended or adjusted under 35 U.S.C. 154(b) by 0 days.

(21) Appl. No.: 09/621,426

(22) Filed: Jul. 21, 2000

(30) Foreign Application Priority Data

Jul. 23, 1999 (JP) .................................................. 11-209995

(51) Int. Cl.[7] .................................................. A61C 7/12
(52) U.S. Cl. .................................................. 433/8
(58) Field of Search .................. 433/8, 9, 10, 16

(56) References Cited

U.S. PATENT DOCUMENTS

| 4,784,606 | * | 11/1988 | Jones et al. | 433/8 |
| 4,988,293 | | 1/1991 | Collins et al. | 433/8 |
| 5,109,586 | * | 5/1992 | Jones et al. | 29/160.6 |
| 5,358,402 | | 10/1994 | Reed et al. | 433/8 |
| 5,380,196 | | 1/1995 | Kelly et al. | 433/8 |
| 5,429,499 | * | 7/1995 | Sernetz | 433/8 |

* cited by examiner

Primary Examiner—John J. Wilson
Assistant Examiner—Melba Bumgarner
(74) Attorney, Agent, or Firm—Kenyon & Kenyon

(57) ABSTRACT

In orthodontic element made of a bracket composed of polycrystalline ceramics, a glass liner is furnished in an archwire slot furnished in the bracket.

13 Claims, 5 Drawing Sheets

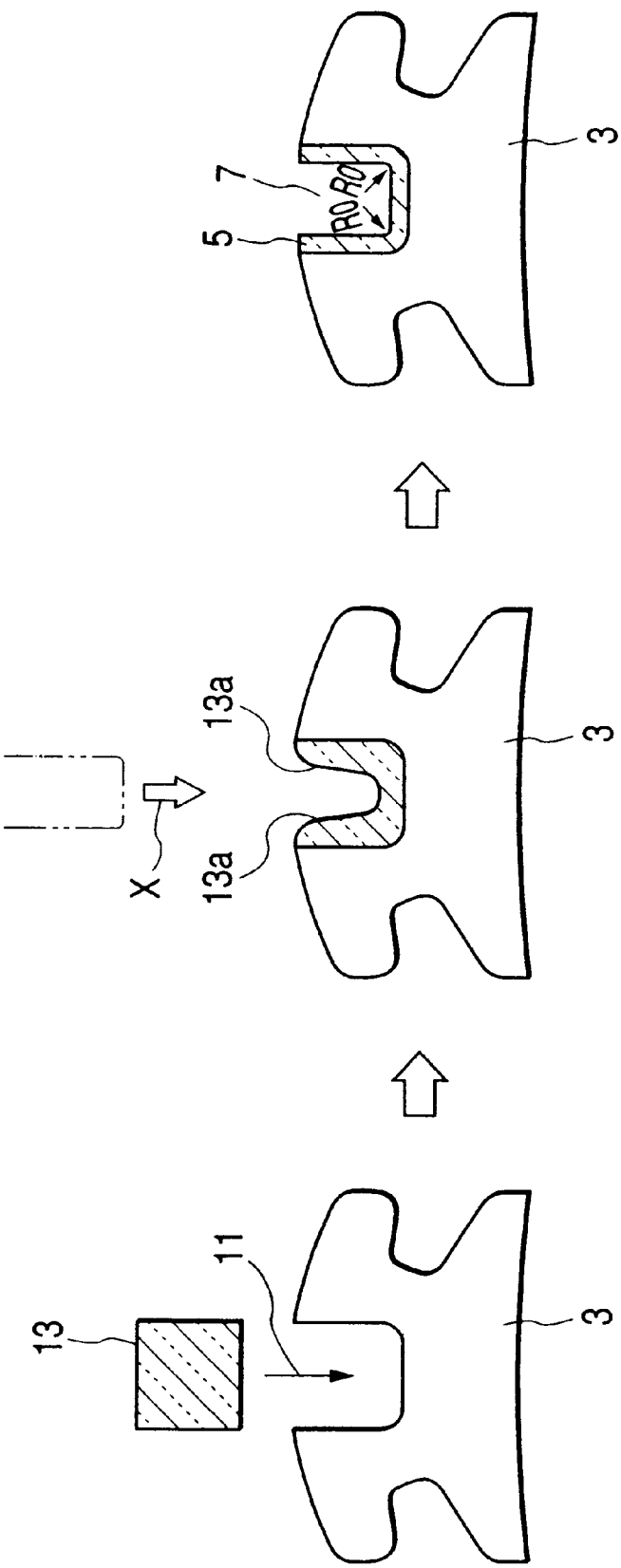

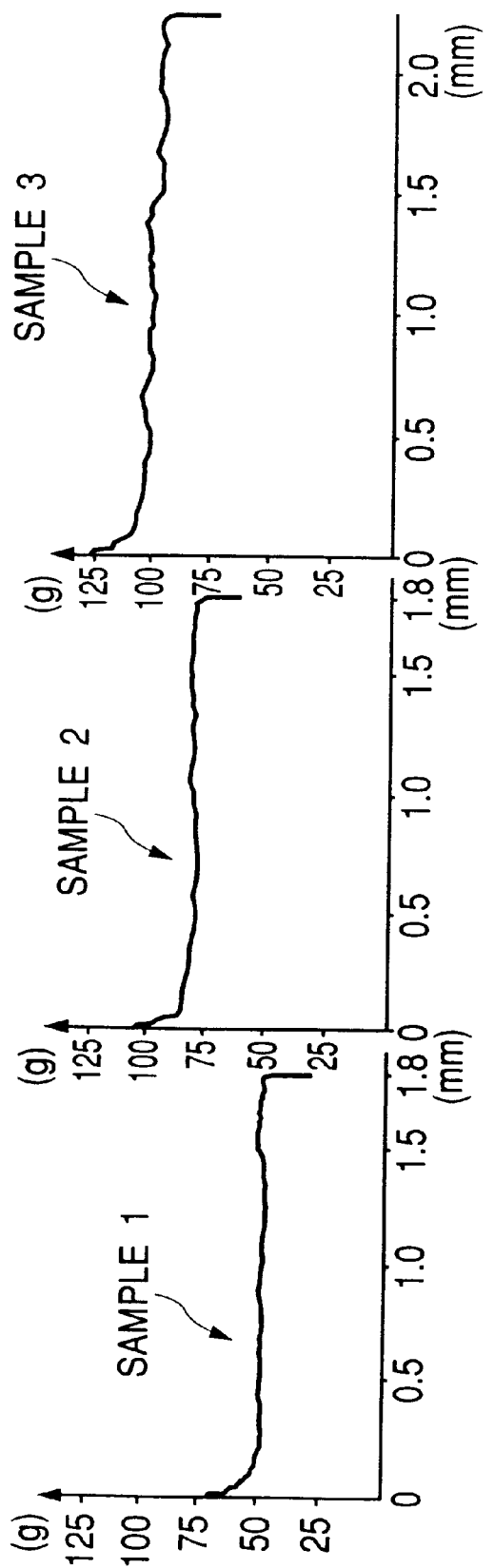

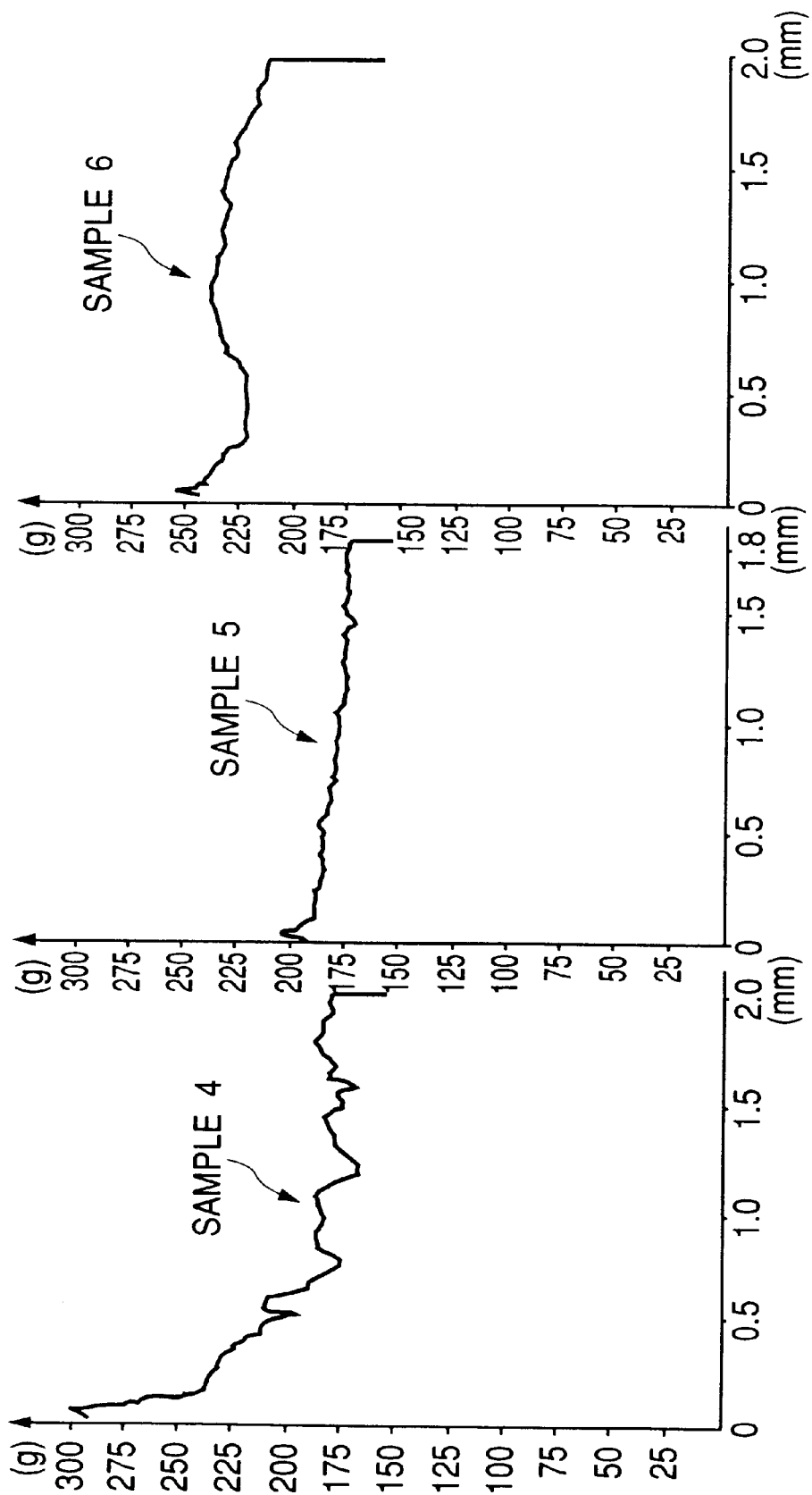

ORTHODONTIC ELEMENT AND MANUFACTURING METHOD

BACKGROUND OF THE INVENTION

1. Field of the Invention

The present invention relates to an orthodontic element and a manufacturing method therefor, and in particular relates to an orthodontic element and a method therefor where the element is furnished with a liner provided inside an archwire slot, in order to improve the slippage and shiftability of archwire engaged in orthodontic brackets made of ceramics.

2. Description of the Related Art

In orthodontic clinical treatment, small implements called brackets are attached to the teeth of the patient. In the past, these brackets were mainly made of metal, but in recent years materials such as plastics and ceramics have been developed in order to improve the aesthetic appearance, and now brackets using ceramics have come into use.

The form of use of these brackets is to attach the brackets to the teeth by adhesion, and in order to impart external force to these brackets intended to straighten the teeth, metal archwire is passed through archwire slots provided in the brackets and the archwire and brackets are suitably tied.

However, ceramic brackets particularly in the case of polycrystalline ceramic brackets have the problem of poor slippage on the metal archwire compared to metal brackets.

That is, many polycrystalline ceramics are made by processing their archwire slots with such as diamond blades so that crystal particles are scarified on the processed surface by such slot processing, making the surfaces rough so that the archwire would not slip.

There exists technology intended to improve the slippage of metal archwire on these types of ceramic brackets, as described for example in U.S. Pat. Nos. 5,358,402 and 5,380,196.

This publication describes that it is possible to turn the friction between the archwire slots and the metal archwire into the friction of metal on metal by furnishing metal liners in the slots provided in the brackets.

Further, U.S. Pat. No. 4,988,293 describes that the strength will be reinforced by providing polycrystalline outer coating layers on brackets comprising monocrystalline alumina, which is very fragile.

In addition to the problems above, ceramic brackets are themselves very hard, so that the metal archwire tends to create friction particularly at mesiodistal ends of the slots. Consequently, there is the problem of archwire slippage being worse at the extreme ends than with metal brackets.

This is equivalent to saying that the bracket is hard to slide on the archwire, with the result that tooth alignment does not proceed, and this leads to the problem of longer periods orthodontic treatment.

In the state of affairs, the structure of the ceramics bracket disclosed in U.S. Pat. Nos. 5,358,402 and 5,380,196, because it uses a metal liner, was a step back aesthetically even though slippage improved. Further, with a structure combining ceramics and metal, joining the ceramics and metal is technologically difficult, and brackets having metal liners had the problem of high cost.

SUMMARY OF THE INVENTION

It is an object of the present invention to improve the slippage of metal archwire and ceramic brackets, together with offering an aesthetically superior orthodontic element and a method for manufacturing it easily.

An orthodontic element according to the present invention is an orthodontic element comprising: a bracket comprising polycrystalline ceramics, in which an archwire engages; and a glass liner provided in an archwire slot formed in said bracket in order to engage the archwire.

In the orthodontic element pertaining to the present invention, said glass liner may be colored, both mesiodistal end surfaces of said archwire slot may be constructed so as to have bevel portions, and the corner radius at the slot bottom surface (the radius of curvature of the R shaped entry angles of the bottom of said archwire slot) are constructed to be 0.03 mm or over.

A method for producing an orthodontic element, comprises the steps of: inserting a glass rod in a slot of a bracket, comprising polycrystalline ceramics whose slot is somewhat larger than the archwire slot required; after the inserting step, melting said glass so that said glass covers the slot internal walls; and forming said glass covering said slot internal walls as a glass liner by processing to a shape nearly along said slot internal walls.

In the method for producing the orthodontic element, hot press processing is used as the processing during the period in which said glass is melted. In the method for producing the orthodontic element, cutting processing is used as the processing after said glass is melted. In the method for producing the orthodontic element, concave portions larger than said slot are previously furnished at both mesiodistal ends of said slot, and when said glass is melted, the glass flows into said concave portions.

Following the orthodontic element pertaining to the present invention, it is an orthodontic element constructed so that archwire engages in a bracket comprising polycrystalline ceramics, and since it is furnished with a glass liner in the archwire slot formed in the bracket for the purpose of engaging the archwire, there is no lowering of slippage between the metal archwire and the bracket, and it is superior aesthetically. Also, by furnishing the glass liner, the strength of the archwire slot portion is increased because glass has a lower stress intensity factor than ceramics, and in particular the fracture toughness is increased when torque is imparted to the bracket by the metal angular archwire (square and rectangular wire).

In the orthodontic element of the present invention, following the structure where the glass liner is colored makes it easy to discriminate the glass liner, for example making it possible to avoid errors by having different colors on respective teeth, and making it easy to determine the positions on tooth surfaces by color.

In the orthodontic element of the present invention, following the structure where both mesiodistal end surfaces of the archwire slot have bevel portions makes it possible to avoid excess friction and gnawing between the archwire and the mesiodistal ends of the archwire slot.

In the orthodontic element of the present invention with the corner radius (R0) at slot bottom surface being constructed to be 0.03 mm or over, when torque is imparted to the archwire, its stress disperses along the archwire slot surface without being concentrated in any one part thereby raising the fracture toughness of the orthodontic element.

Following the method of manufacturing the orthodontic element pertaining to the present invention, it is a method of making orthodontic elements using brackets comprising polycrystalline ceramics, and after glass rod is insert in a slot of the bracket whose slot is somewhat larger than the archwire slot required, said glass is melted so as cover the slot internal walls by capillary action so that the glass and ceramics are chemically bonded, and said glass covering said slot internal walls is formed as a glass liner by processing to a shape nearly along said slot internal walls, so as to be able easily to manufacture an orthodontic element that is aesthetically superior without lowering the slippage between the metal archwire and the bracket.

Also, within the method of manufacturing said orthodontic element pertaining to the present invention, forming of the liner is very easy with the method using hot press forming for processing during the glass is melted, making it a manufacturing method suitable for mass production.

Also, within the method of manufacturing said orthodontic element pertaining to the present invention, forming of the liner can be done individually as required with the method using grinding process after the glass is melted.

Also, within the method of manufacturing said orthodontic element pertaining to the present invention, it is possible to previously furnish concave portions larger than said slot at both ends of said slot, so when said glass is melted the glass flows into said concave portions so as to easily form a liner having roundness in the portions on both mesiodistal ends.

BRIEF DESCRIPTION OF THE DRAWINGS

In the accompanying drawings:

FIG. 1A shows an upper surface view of the orthodontic element, FIG. 1B shows a side surface view, FIG. 1C is a side surface view showing orthodontic elements having a torque-in-base structure, and FIG. 1D is a side surface view having a torque-in-face structure;

FIGS. 2A to 2C are explanatory diagrams showing a method for manufacturing the orthodontic element pertaining to the present invention;

FIGS. 5A to 5C are graphs showing the friction resistance of samples 1 through 3 in the example; and FIGS. 6A to 6C are graphs showing the friction resistance of samples 4 through 6 in the example.

PREFERRED EMBODIMENTS OF THE INVENTION

Preferred embodiments according to the present invention will be explained in detail with reference to the accompanying drawings.

Figure 1A:
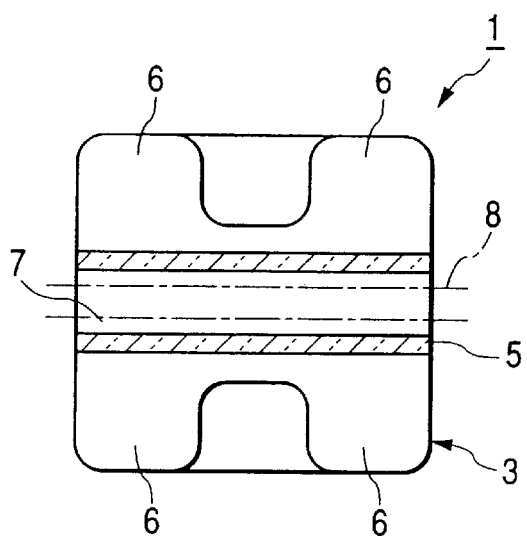
FIGS. 1A to 1D are explanatory diagrams of an embodiment of an orthodontic element pertaining to the present invention.
Figure 1B:
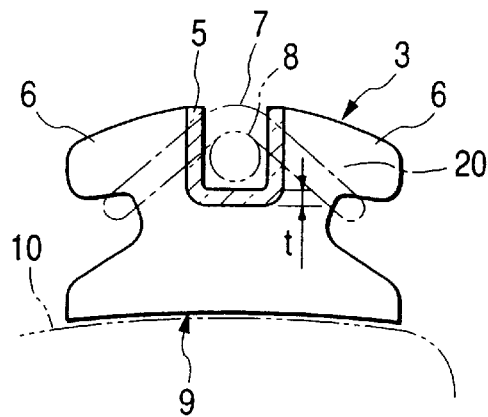

FIGS. 1A and 1B shows an embodiment of the present invention. Further, FIG. 1A is an upper surface view of a orthodontic element 1, and FIG. 1B is a side surface view.

The orthodontic element shown in FIGS. 1A and 1B is composed of polycrystalline ceramics, being a bracket 3 whose side opposite the lower bottom side towards the tooth has an archwire slot 7 formed in the mesiodistal direction for containing an archwire 8 and tie wings 6 projecting on the gingival and occlusion sides. In this archwire slot 7, a glass liner 5 is formed so as to coat the slot 7.

The bracket 3 constructed in this manner, as is well known, is attached on its tooth side lower surface 9, which is the bonding base surface, to a tooth 10 with adhesive. Then, a metal archwire 8 is engaged in the archwire slot 7, and the archwire slot 7 and archwire 8 are tied with a ligature wire or an elastomeric ligature ring 20.

In this embodiment, as the above glass liner 5 is provided in the archwire slot 7 of the ceramics bracket 3 so that there will be good slippage between the archwire 8 and the archwire slot 7. Also, since there is transparency (or translucency) because the glass liner 5 is present, the aesthetics will also be superior.

Thickness (t) of the glass liner 5 is not particularly restricted, but about 50 to 100 $\mu$m, for example, would be preferred.

In this embodiment, the polycrystalline ceramics serving as the bracket 3 preferably can have a structure made of polycrystalline alumina ($Al_2O_3$) or zirconia ($ZrO_2$). So this bracket 3 is capable of using substances with optical transparency or translucency (light can pass through).

Also, the slot liner is preferred to form to include considerable silica ($SiO_2$). It is possible to use such as for example soda lime glass or borosilicate glass as the glass types used in the glass liner 5. There will be good slippage for the metal archwire 8 because the glass liner 5 is amorphous.

Also, the material for the glass liner 5 should have a small coefficient of friction, and crystallized glass for example can be used. This crystallized glass will have as its main ingredients, for example, silica ($SiO_2$), alumina ($Al_2O_3$), lithium oxide ($Li_2O_3$), titanium oxide ($TiO_2$) or zirconia ($ZrO_2$), and after first being formed as glass it is reheated, so that the crystals in the glass are precipitated, giving its properties closer to stone than glass and making a smaller coefficient of friction possible.

The glass liner 5 can be colorized to allow discrimination. For example, mistakes in use can be prevented by color-coding specifically for the tooth 10, making it easy to determine the position on the tooth surface by the colorization, and the colored glass liner 5 works as a guideline for the archwire slot 7.

Figure 1C:
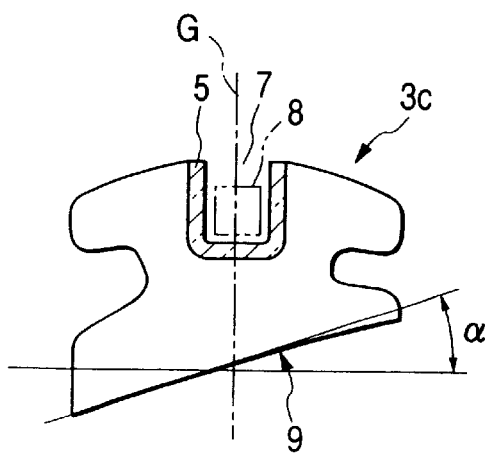

As a modification of this embodiment of the present example, a bracket 3c as shown in FIG. 1C can have its tooth side bottom surface with a torque-in-base structure. This torque-in-base structure is one having a certain fixed angle on the bottom surface 9 relative to the surface formed by the archwire slot 7 (it has inclination angle $\alpha$ in respect to the axis at right angles to center line G in the direction of the depth of the archwire slot 7). That is, the angular archwire 8 with an angular section as illustrated in FIG. 1C is in a state where it imparts pressing of the bracket 3c toward the tooth surface side, so that it can apply inclined force in the desired direction against the tooth (the archwire 8 can impart torque directly to the bottom and the side surface of the archwire slot 7).

Figure 1D:
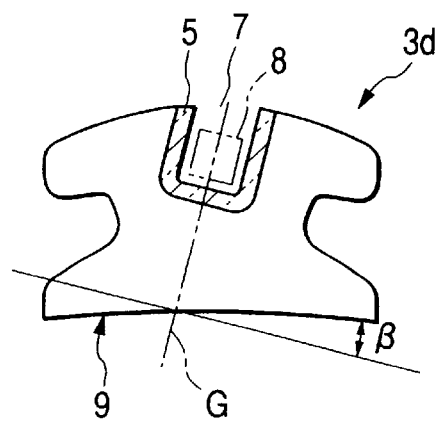

Also, as another modification, as shown by the torque-in-face structure illustrated in FIG. 1D, the archwire slot 7 is one that has a certain fixed angle relative to the tooth side bottom surface 9 (the axis at right angles to center line G in the direction of the depth of the archwire slot 7 has inclined angle $\beta$ relative to the bottom surface 9). In this case also, the angular archwire 8 is in a state where it imparts pressing of a bracket 3d toward the tooth surface side, so that it can apply inclined force against the tooth in the required direction.

Next, a method for manufacturing the orthodontic element of the present invention will be explained with reference to FIGS. 2A to 2C.

Further, in the present specification, a state where the glass liner is formed is called "archwire slot 7", and a state before the glass liner is formed is called "slot 11".

First, the bracket 3 having a slot 11 somewhat larger than the desired archwire slot 7 is prepared.

The glass rod 13 previously formed, for example at 700° C., is inserted into this slot 11. The term previously formed as used here means that a glass rod with an angular sectional shape is previously made in a heating atmosphere of 700° C. using a special metal mold. (See in FIG. 2A)

Then the bracket 3 with the glass rod 13 inserted into the slot 11 passes through a 1,100° C. reduction atmosphere. As a result, as illustrated in FIG. 2B, a glass coating 13a from the melted glass rod 13 coats the slot inner walls of the slot 11.

After this, using a press head of the required shape, the glass coating 13a is suitably compressed (compression in the direction of arrow X) under the condition that the heated glass is still soft, so that as shown in FIG. 2C, it is possible to form the glass liner 5 of the required shape.

Also, as another processing method, it is possible, after coating the slot inner walls of the slot 11 with the glass coating 13a, to do plastic forming of the glass coating 13a coated on the slot inner walls with, for example, a narrow diamond blade (not illustrated). When processing by this method, it is possible to form the glass liner 5 having the archwire slot 7 to the desired shape with good accuracy.

Further, the internal angles of the bottom of the archwire slot are processed so that the corner radius (R0) Of its R shape of 0.03 mm or over. Consequently, when imparting torque to the archwire the stress can be suitably dispersed, giving a fracture toughness that is higher than the brackets without said R shape. Incidentally, if the corner radius (R0) of the R shape is smaller than 0.03 mm, there is little stress dispersion function.

Figure 3A:
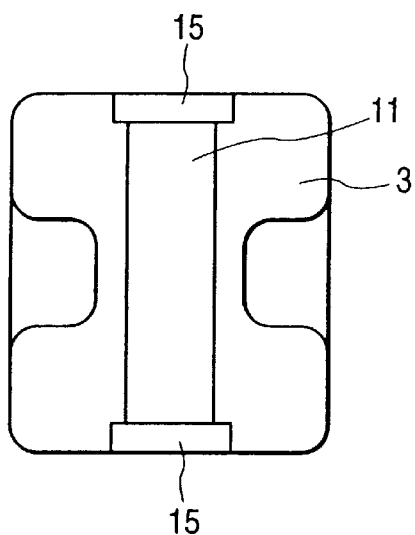
FIGS. 3A to 3C are explanatory diagrams showing another embodiment of the orthodontic element pertaining to the present invention.
Figure 3B:
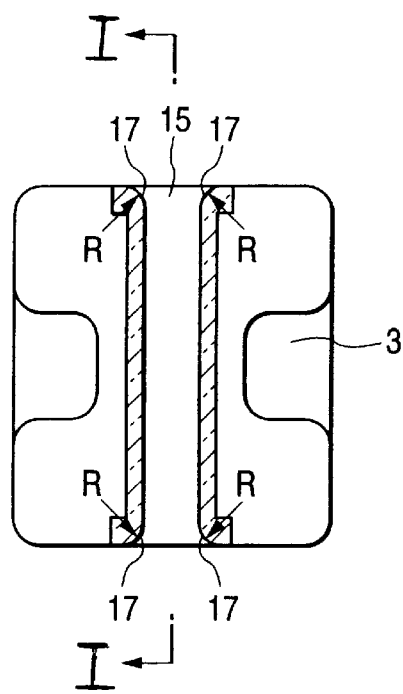
Figure 3C:
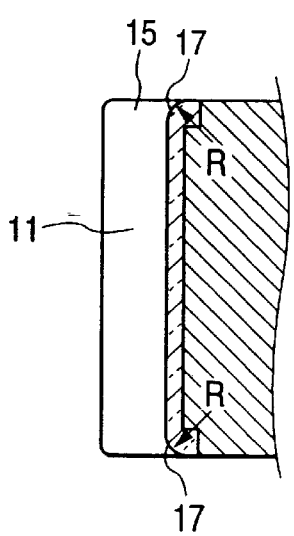

Also, another method of the processing is for example to previously provide concave portions having a size larger than slot 11 on both mesiodistal ends of the slot 11 of the bracket 3 as illustrated in FIG. 3A. Providing these concave portions 15 makes it possible to give the glass bevel portions 17 (rounded surfaces) at both ends as illustrated in FIG. 3B, when melting the glass to coat the inner walls of the slot 11. Further, as shown in sectional view of FIG. 3C (section along line I—I in FIG. 3B), the structure is such that the rounded shapes at both ends go around the entire edges of the slot 11.

These bevel portions 17 can be formed accurately by the above mentioned hot press processing, and can also be made with good precision by, for example, cutting processing and wet sand blasting. Further, the R dimensions of cut of the bevel portions 17 can be for example on the order of 0.05 mm to 0.5 mm.

Also, the bracket 3 pertaining to the present invention is made of polycrystalline ceramics with crystal particle diameters of 10 to 100 $\mu$m. Since there is a glass material (amorphous portion) in the crystal grain boundaries of the ceramics surface (the slot 11 surface), the result is good adhesion between the glass liner surface 5 and the polycrystalline ceramics surface. Consequently, furnishing the glass liner increases the strength of the archwire slot portion and raises fracture toughness.

The effect of the present invention can be made apparent next by means of examples.

EXAMPLE 1

Brackets were tested for frictional force. A materiel of the bracket used in Example 1 was $Al_2O_3$. A material of the glass liner used in Example 1 was $Na_2O.BaO.SiO_2$ type. The thickness of the glass liner at bottom portion was 100 $\mu$m and that of the glass liner at wall portion was 50 $\mu$m. Glass was added to concave portions at both mesiodistal ends so as to form the bevel portions at about 0.2 mm corner radius.

Frictional forces were compared for brackets furnished with glass liners (Samples 1, 2 and 3) and brackets without glass liners (Samples 4, 5 and 6).

Figure 4:
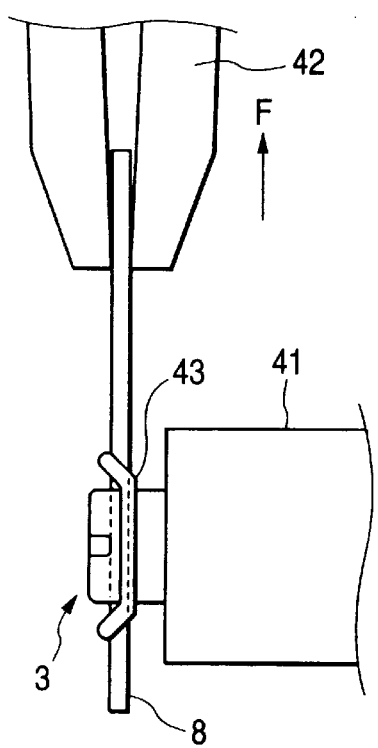
FIG. 4 is a partially abbreviated diagram showing a method of measuring the friction resistance in an example of the present invention.

The method of frictional force testing was, as illustrated in FIG. 4, to fasten the bracket 3 with adhesive to a fastening element 41, an insert stainless angular archwire 8 (0.018 inch×0.025 inch) into the archwire slot of the bracket 3, and put it in a tied state with an elastometric ligature ring 43. In this state, the angular archwire 8 was held and pulled using a chuck 42, and variations in drawing force at this time were measured.

<Test Conditions>

Brackets used were lower anterior tooth brackets (AN).

Tensile rate of 8 mm/min.

Temperature of 37° C.

Wet conditions.

The test results are shown in FIGS. 5 and 6.

As will be understood from FIGS. 5A to 6C, there was large drawing resistance (friction force) in the brackets without glass liners (samples 4 to 6) in the range of 175 to 225 g, and further, the fluctuation of the resistance (friction) variation line was large. On the other hand, in the brackets (samples 1 to 3) with glass liners (samples 1 to 3), the drawing resistance (friction force) was small in the range of 50 to 100 g, and the fluctuation of the resistance (friction) variation line was small.

EXAMPLE 2

Bracket fracture toughness (torque rupture strength) was tested. A bracket used in this example is the same as Example 1.

Tests were made by imparting rotational torque with the rectangular archwire to brackets without glass liners (Samples 7 and 8) and to brackets furnished with glass liners 0.65 mm thick (Samples 9 and 10).

Two types of rectangular archwire were used, being full size cobalt chromium alloy wires that were 0.018 inch (actual rectangular dimensions of 0.018 inch×0.025 inch) and 0.022 inch (actual rectangular dimensions of 0.0215 inch×0.028 inch).

Torque tests were made by fixing each bracket, inserting the rectangular archwire into the archwire slot of the bracket so that both ends of the archwire were in a fastened state and tying up with respect to the bracket (using an elastometric ligature ring). Then rotational torque was applied around the axis of the rectangular archwire, and the torque was measured when the bracket slot bottom (bonding base side from the slot lower side portion) fractured (crack generated).

Further, Comparative Sample 7 and Working Sample 9 used lower anterior tooth brackets (AN) with archwire slots 0.018 inches wide, while Comparative Sample 8 and Working Sample 10 used upper canine brackets (UCS) with archwire slot width of 0.022 inch.

The test results are given in Table 1. As will be understood from Table 1, the brackets pertaining to the present invention furnished with glass liners had strengths about 1.3 to 1.5 times those of the ones not furnished with glass liners.

TABLE 1

| Test Sequence: | | First Bracket | Second Bracket | Third Bracket |
| --- | --- | --- | --- | --- |
| (AN) 0.018 Inch Archwire Slots | Comparative Sample 7 | 660 | 640 | 660 |
| | Working Sample 9 | 840 | 890 | 890 |
| (UCS) 0.022 Inch Archwire Slots | Comparative Sample 8 | 650 | 710 | 550 |
| | Working Sample 10 | 1070 | 910 | 860 |

(Units: gf · cm)

As described above, by following the orthodontic element pertaining to the present invention, a glass liner is applied to an archwire slot provided in a ceramics bracket, which not only gives good slippage between the metal archwire and the bracket, but also makes it possible to have an orthodontic element that is superior aesthetically. Further, providing a glass liner makes it possible to offer an effect where the fracture toughness of the ceramics bracket is increased.

Also, by following a structure where the glass liner is colored makes it easy to discriminate among glass liners, for example making it possible to avoid errors by using different colors for different teeth, therefore making it possible to offer an orthodontic element of superior handling capability and which is easy to position on the tooth surface because of the coloration.

Also, with the orthodontic element pertaining to the present invention, following a structure such that both mesiodistal end surfaces of the archwire slot have bevel portions makes it possible to prevent excessive friction and gnawing phenomena between the archwire and both ends in the mesiodistal direction of the archwire slot, so that teeth shifting progresses smoothly, and it is possible to offer an orthodontic element capable of shortening the orthodontic treatment period.

Following the orthodontic element pertaining to the present invention makes it possible to offer an orthodontic element that, when the corner radius at the slot bottom surface are 0.03 mm or over, raises the fracture toughness by making stress dispersion possible at times when archwire torque is imparted.

Following the method of manufacturing the orthodontic element pertaining to the present invention, it is possible to make an orthodontic element that is superior both functionally and aesthetically by easy methods of glass melting and processing.

Also, relying on hot press processing as the processing after the glass has been melted makes it possible to offer an orthodontic element whose glass forming is very easy and that is suitable for mass production.

Still further, within the orthodontic element pertaining to the present invention, by previously providing concave portions on the mesiodistal ends of the slot that are larger than said slot so that glass flows into the concave portion while the glass is melted, it is possible to easily form a liner having roundness in portions of the mesiodistal ends, and it is further possible to offer a method of manufacturing an orthodontic element with good slippage.

What is claimed is:

1. An orthodontic element comprising:

a bracket comprising polycrystalline ceramics, in which an archwire engages; and a glass liner provided in an archwire slot formed in said bracket in order to engage the archwire.

2. The orthodontic element described in claim 1, wherein said glass liner is colored.

3. The orthodontic element described in claim 1, wherein both mesiodistal end surfaces of said archwire slot have a bevel portion.

4. The orthodontic element described in claim 1, wherein the corner radius at the slot bottom surface is constructed to be 0.03 mm or over.

5. The orthodontic element described in claim 1, wherein said polycrystalline ceramics comprises at least one of polycrystalline alumina ($Al_2O_3$) or zirconia ($ZrO_2$).

6. The orthodontic element described in claim 1, wherein said bracket comprises substances with optical transparency.

7. The orthodontic element described in claim 1, wherein said bracket has its tooth side bottom surface with a torque-in-base structure.

8. The orthodontic element described in claim 1, wherein said bracket comprises substances with optical translucency.

9. The orthodontic element described in claim 1, wherein said bracket comprises polycrystalline ceramics with crystal particle diameters of 10 to 100 µm.

10. A method for producing an orthodontic element, comprising the steps of:

inserting glass in a slot of a bracket, comprising polycrystalline ceramics, whose slot is somewhat larger than the archwire slot required;

melting said glass so that said glass covers the slot internal walls; and forming said glass covering said slot internal walls into a glass liner by processing to a shape nearly along said slot internal walls.

11. The Method for producing the orthodontic element described in claim 10, wherein hot press processing is used as the processing after said glass is melted.

12. The method for producing the orthodontic element described in claim 10, wherein cutting is used as the processing.

13. The method for producing the orthodontic element described in claim 10, wherein concave portions larger than said slot is previously furnished at both ends of said slot, and when said glass is melted, the glass flows into said concave portions.

* * * * *